US012653393B2

(12) United States Patent
Napier

(10) Patent No.: US 12,653,393 B2
(45) Date of Patent: Jun. 16, 2026

(54) DISPOSABLE VIDEO LARYNGOSCOPE WITH FLUID SPRAY SYSTEM

(71) Applicant: Intublade Co., Odessa, FL (US)

(72) Inventor: Andrew B. Napier, Miami, FL (US)

(73) Assignee: Intublade Co., Odessa, FL (US)

( * ) Notice: Subject to any disclaimer, the term of this patent is extended or adjusted under 35 U.S.C. 154(b) by 152 days.

(21) Appl. No.: 18/181,179

(22) Filed: Mar. 9, 2023

(65) Prior Publication Data

US 2023/0277051 A1 Sep. 7, 2023

Related U.S. Application Data

(60) Continuation of application No. 17/389,254, filed on Jul. 29, 2021, now Pat. No. 11,627,873, which is a division of application No. 16/352,723, filed on Mar. 13, 2019, now Pat. No. 11,103,130.

(51) Int. Cl.
| | |
|---|---|
| *A61B 1/267* | (2006.01) |
| *A61B 1/00* | (2006.01) |
| *A61B 1/05* | (2006.01) |
| *A61B 17/00* | (2006.01) |

(52) U.S. Cl.
CPC .............. *A61B 1/267* (2013.01); *A61B 1/05* (2013.01); *A61B 1/00119* (2013.01); *A61B 2017/0023* (2013.01)

(58) Field of Classification Search
CPC .................................................. A61B 17/267
See application file for complete search history.

(56) References Cited

U.S. PATENT DOCUMENTS

| | | | | |
|---|---|---|---|---|
| 2007/0293726 A1* | 12/2007 | Goldfarb | ................ | A61B 1/233 |
| | | | | 600/178 |
| 2012/0316395 A1* | 12/2012 | Koga | ................. | A61B 1/00101 |
| | | | | 600/157 |
| 2014/0360494 A1* | 12/2014 | Herskovic | ............ | A61M 11/007 |
| | | | | 128/200.26 |
| 2015/0099934 A1* | 4/2015 | Sartore | ............. | A61M 16/0486 |
| | | | | 600/187 |
| 2016/0256047 A1* | 9/2016 | Newcomb | ............ | A61B 1/0684 |
| 2019/0223694 A1* | 7/2019 | Lund | ................. | A61B 1/00066 |

* cited by examiner

*Primary Examiner* — Tessa M Matthews
(74) *Attorney, Agent, or Firm* — SLEMAN & LUND LLP

(57) ABSTRACT

A disposable video laryngoscope includes a novel internal liquid jet spray. This laryngoscope is designed so that the user may utilize either the video mode in which the image is displayed on an external screen, or the device may be used in the same manner as a direct laryngoscope. If the device is used in video mode, a Light Emitting Diode (LED) is placed within a camera housing so as to prevent or reduce fogging of the lens. The device includes an internal spray mechanism that may receive liquid through a luer-connection interface such as is used with syringes or IV tubing systems and that directs a spray onto a fogged or occluded lens to restore vision.

9 Claims, 3 Drawing Sheets

DISPOSABLE VIDEO LARYNGOSCOPE WITH FLUID SPRAY SYSTEM

CROSS-REFERENCE TO RELATED APPLICATIONS

The present application is a continuation of U.S. patent application Ser. No. 17/389,254, filed Jul. 29, 2021, which is a divisional of U.S. patent application Ser. No. 16/352, 723, filed Mar. 13, 2019, filed Mar. 13, 2019, now U.S. Pat. No. 11,103,130, the disclosure of which is hereby incorporated in its entirety as if fully set forth herein.

FIELD OF THE INVENTION

The invention relates to a disposable video laryngoscope that contains an internal liquid jet delivery system that the user may utilize to optimize the view. The device is designed so that it may also be used in either video mode or as a direct laryngoscope. When used in video mode, a Light Emitting Diode (LED) is placed within a camera housing so as to prevent or reduce fogging of the lens. The device includes an internal spray mechanism that may receive liquid through a luer-connection interface such as is used with syringes or IV tubing systems and that directs a spray onto a fogged or occluded lens to restore vision.

BACKGROUND OF THE INVENTION

There are numerous medical scenarios in which a patient must be externally ventilated in order to provide oxygenation. The delivery of the oxygen may be accomplished through the use of an endotracheal tube. An endotracheal tube is inserted into the throat after the patient is sedated and then sometimes chemically paralyzed for a short length of time, in a procedure known as endotracheal intubation. An endoscope is typically used to clear the passageway sufficiently to allow insertion of the tube. Typically, this is done by placing the blade against the tongue at the rear of the mouth and, while moving the tongue to the side, is leveraged to hold (compress) the tongue and throat tissue sufficiently to create an open passageway. This procedure requires the operator to move at an accelerated pace and under great pressure as a patient who is sedated and chemically paralyzed is unable to initiate respirations unassisted.

As medical advancements have continued in this field over the last few decades, a type of laryngoscopy has emerged known as the video laryngoscopy. This camera-based system allows the operator to quickly identify the proper anatomy displayed on an external screen which is needed in order to be successful in this procedure. However, these systems differ in their design and function from the gold standard of teaching endotracheal intubation which is by use of direct laryngoscopy. Many of the video laryngoscope systems are designed to include a hyperangulated blade system that requires the use of specialized stylets which are placed into endotracheal tubes. This requires additional training and familiarity with video-based systems which may vary in each institution and which may also include the need to purchase specialized stylets. In addition, if the video function fails then the entire video laryngoscope system must be abandoned as most are designed to operate solely in video mode. This poses disadvantages to the operator, the patient, and the purchasing party of the medical equipment as valuable time may be lost during this procedure by unskilled operators, and additional costs may be incurred by the purchaser who is required to also purchase specialized stylets.

Another disadvantage of many video laryngoscopy systems stems from the risk of unintended spread of infectious disease amongst patients. For example, endotracheal intubation can at times be an uncleanly procedure in which the operator and the operator's equipment are exposed to various bodily fluids. This equipment may be cleaned and sterilized to a certain degree but if improper technique is utilized or the pathogen causing infectious disease is resistant to the method of cleaning, then subsequent patients are clearly at risk for spread of said infectious disease.

Yet another disadvantage that operators of traditional video laryngoscopes face is that the camera lens may easily be obscured by bodily fluids or by fogging during the procedure. Certain instances such as providing medical support on the battlefield or during prehospital care with paramedics may present unique situations in which the visual field of a video laryngoscope can become obstructed. In the event of an obscured view, the operator is required to remove the intubating device from the patient's oropharynx, clean the lens, re-oxygenate the patient, and then attempt to locate the appropriate anatomy again. This may add more time for the procedure while the patient's level of oxygenation decreases, and the patient's status will continue to decompensate further. This process, therefore, is not ideal as many attempts may be required in order to achieve a successful endotracheal intubation.

SUMMARY OF THE INVENTION

It is an object of the invention to provide a video laryngoscope having a design that is similar to traditional direct laryngoscopes to reduce additional training of staff.

It is another object of the invention to provide a video laryngoscopy system at is disposable and will thereby reduce the spread of infectious disease by eliminating the recurrent use of video laryngoscopes that may have residual contamination.

It is a further object of the invention to create a video laryngoscope that does not require the use of specialized stylets.

It is yet another object of the invention to provide a video laryngoscope that contains an integral system to clean and de-fog its imaging apparatus so that adequate visualization is maintained at all times.

The video laryngoscope of this invention is modeled after the direct laryngoscope which provides an operator the flexibility and comfort of using a singular technique for endotracheal intubation awhile simultaneously having the capability of using direct visualization or the ability to utilize a camera for a digital image.

When used in video mode, a Light Emitting Diode (LED) is placed within a camera housing so as to prevent or reduce fogging of the lens. The device includes an internal spray mechanism that may receive liquid through a luer-connection interface such as is used with syringes or IV tubing systems and that directs a spray onto a fogged or occluded lens to restore vision.

In an embodiment, the laryngoscope is built as a single unit that does not require the assembly of components and is designed to be single use only. The preassembly of the laryngoscope allows for reduced time needed for preparation for this procedure and eliminates the risk of missing components. The disposable nature of the device reduces the burden on facility resources and removes the risk of unintended spread of disease among subsequent patient encounters with the device. In other embodiments, the head and handle may be separate units that are combined for use such that a single handle containing a liquid reservoir, or an electronic module and battery may be used with any number of disposable heads.

To help optimize visualization, the laryngoscope includes a liquid jet spraying system to clean the camera lens with a small amount of liquid solution while the device is within the oropharynx. The internal liquid channel within the device is narrow so as to require minimal pressure from the operator and to minimize the amount of liquid needed to clean the lens. These narrow channels are connected by secure rubber tubing and are positioned so that the device will not leak fluid when positioned upright. The liquid jet is sprayed from beneath the camera itself without obstruction of view.

Further features and advantages of this device will be apparent from the following detailed descriptions and drawings.

DETAILED DESCRIPTION OF THE PREFERRED EMBODIMENTS

Figure 1:
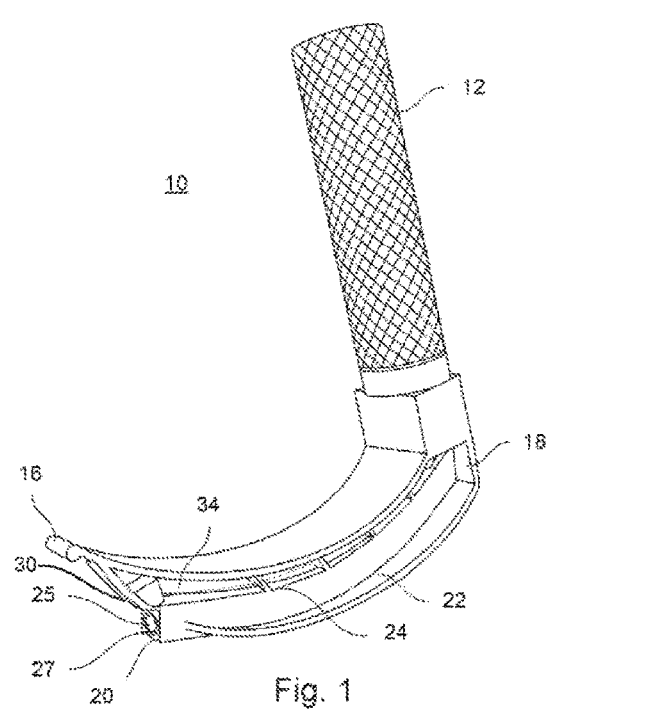
FIG. 1 is an isometric right view of the laryngoscope of this invention depicted in FIG. 4.

Referring now to the drawings, wherein like reference numerals designate corresponding structure throughout the views.

Figure 2:
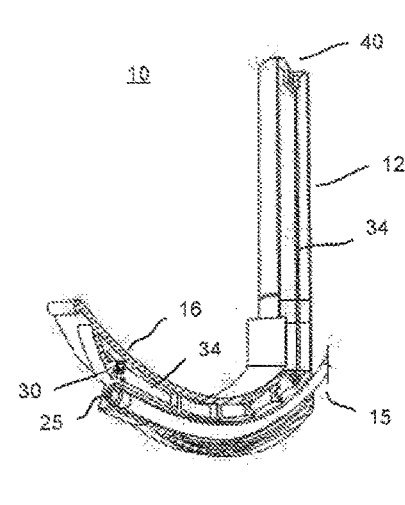
FIG. 2 is a sectional view of the laryngoscope of this invention taken along sectional line A-A of FIG. 4.

In FIGS. 1 and 2, the laryngoscope 10 is comprised of an integral unit consisting of a handle 12 and a blade 16 that are in a fixed position. The laryngoscope includes an endoscopic camera or imaging device 25 that is connected to a camera cable 15. The imaging device includes a source of illumination within its housing 20 in the form of one or more LEDs 27, as is shown in greater detail in FIG. 8.

Figure 3:
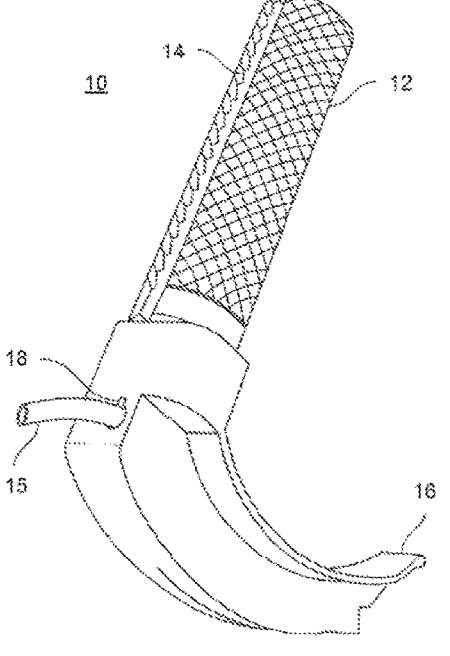
FIG. 3 is an isometric, left rear view of the laryngoscope of this invention.
Figure 4:
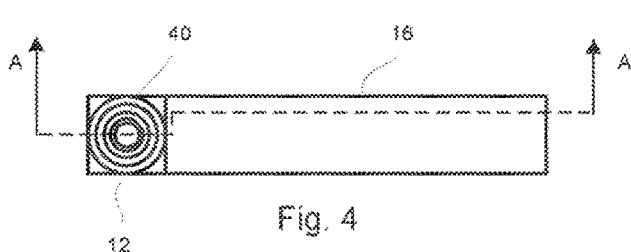
FIG. 4 is a plan view of the laryngoscope of this invention showing sectional line A-A.

FIG. 3 is a rear view of the laryngoscope which illustrates the insertion point 18 of the multiplewire camera cable 15 which may extend directly from the insertion point 18 to an external monitor. As is shown in FIG. 3 the handle 12 may have a posterior groove 14 into which the camera cable 15 may inserted, if desired. The cable 15 may be slightly oversized for the groove 14 and when pressed into the groove will remain flush and secure within the groove and out of the operator's way. This allows for increased autonomy for the operator who is thereby given two options to arrange the cable so as not to interfere with the procedure being conducted. The cable 15 connects to or communicates with an external monitor, and will provide power to both the imaging and illumination sources for the video component via the cable 15.

Referring to FIGS. 5-8, an imaging system is located near the end of the blade 16 and is situated within a housing 20 located within a walled-off move 22 inside the blade. The imaging system includes an endoscopic camera 25 situated within the housing 20 having a lens 32, and that is surrounded by LEDs 27 that serve the dual purpose of heating the lens 32 to reduce condensation and of illuminating tissue directly proximate to the blade of the laryngoscope. The camera 25 is connected directly to camera cable 15 which is carries a video signal received by an external monitor.

A difficulty that an operator mayace when attempting to obtain ideal views for the intubation procedure is that of a fogged lens of the endoscopic camera. To prevent fog and to provide illumination, LEDs 27 are built within the endoscopic camera housing 20 so as to provide a heated window and ensure that the illumination is near the intended target. The LEDs and endoscopic camera combination are placed within the device and are securely held in position.

Figures 5, 6, 7, 8:
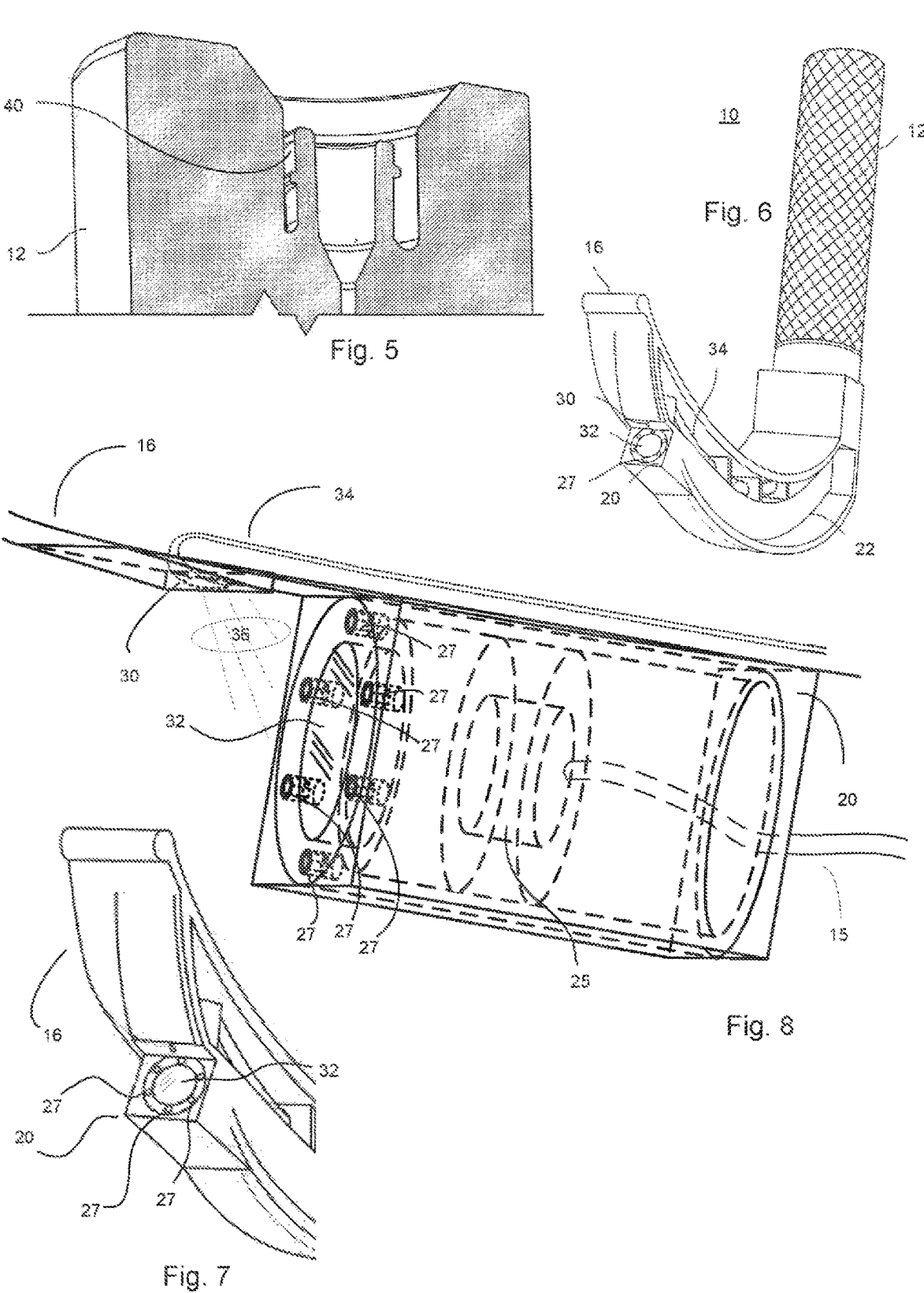
FIG. 5 is a sectional view of the distal end of the handle of the laryngoscope of this invention taken along sectional line A-A showing the luer-fitting connector.
FIG. 6 is an isometric right view of the laryngoscope of this invention depicted in FIG. 1.
FIG. 7 is an enlarged image of the end of the blade in FIG. 6.
FIG. 8 shows internal detail of the housing component of FIG. 7.

The LEDs 27 are the source of illumination for the camera which, for purposes of defogging the lens 32, may be located adjacent the lens. In FIGS. 7 and 8, the LEDs 27 are located within the housing 20 of the imaging device and provide illumination for the image being sent to the external monitor. Power is provided to the LEDs through the multiple-wire camera cable 15. The activated LEDs 27 produce heat within the housing 20, thus reducing or eliminating any fog and condensation that may form on the lens and compromise an operator's view of the tissue being encountered by the laryngoscope.

The endoscopic camera 25 is located within the posterior aspect of the blade and assumes the correct orientation by a guide that is bossed onto the camera. The camera is held securely in place within a housing 20 built into the blade and the cable 15 may be run up the back of the handle into the groove 14 or it pray extend from the posterior aspect of the blade depending on the operator's preference and/or clinical scenario. The camera is then securely fastened via sturdy threaded cable.

The laryngoscope of this invention also includes an attachment port 40 for a luer-compatible device which accepts a connection to a fluid reservoir which provides fluid to clean the lens 32. The end of the handle 12 contains a luer-fitting connector 40 which is flush with the base of the handle. FIG. 5 depicts a sectional view of the bier connection 40 that is integrated into the handle 12 of the laryngoscope. Fluid enters the handle from an external source such as a luer-compatible syringe or IV tubing and travels through the luer connection 40 into tubing 34 located the laryngoscope's handle 12. As depicted in FIGS. 1 and 2, the tube 34 is coupled at either end via tube connectors 17 and situated within the guides 24 built into the blade of the device. The fluid travels through the handle and blade of the laryngoscope to a nozzle 30 from which it will be forcefully sprayed onto the lens 32. The fluid exits the nozzle as a jet (shown as 36 in FIG. 10 but which does not comprise part of the invention) and strikes the lens centrally in order to clear obstructions to the view of the image. In an embodiment shown in FIG. 2, the laryngoscope has an internal tube 34 that runs from the luer connection 40 to the nozzle 30 to deliver a spray to the lens 32. In this embodiment, an operator can actuate the spray by operating a foot pedal or some other fluid pressurization mechanism known in the art (not shown) to deliver a liquid spray through the tube 34 and onto the camera lens 32 for the purpose of clearing the visual field. The luer-fitting connector 40 within the handle is compatible with syringes and IV tubing connectors that utilize the luer-connection interface. The internal tube 34 is sized to cause a small amount of fluid to be expelled from the nozzle 30 with sufficient force to clear the visual field of the lens of the camera.

In the drawings the laryngoscope is shown with an upward curving blade such as the traditional Macintosh kyle blade but can also be produced with a straight blade such as the traditional Miller design without compromising the features of the invention claimed herein. The system is composed of rigid plastic that is intended for disposal, but the system is not limited to this option.

The liquid jet spraying system is compatible with multiple delivery systems within a healthcare setting due to its leer-fitting connector. This connector is compatible with many commonly used leer-connection interfaces such as syringes, IV extension tubing, or even IV tubing connectors, thereby allowing for flexibility and ease of choice for the operator depending on the clinical scenario.

Figure 9:
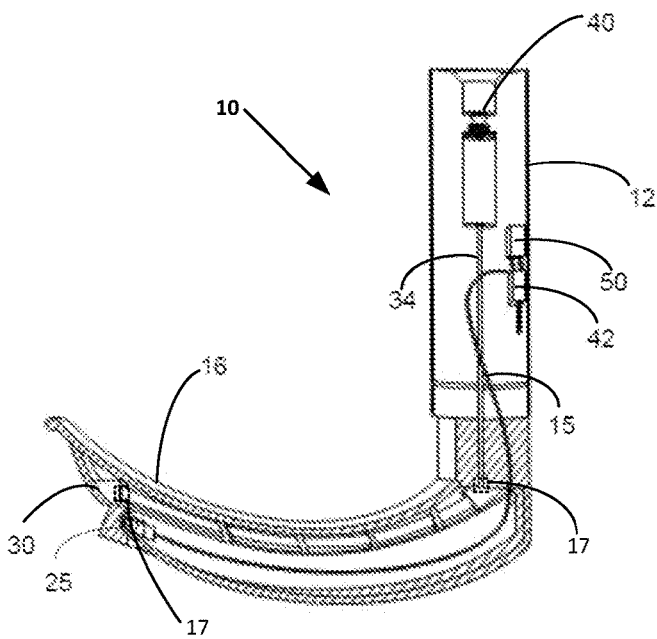
FIG. 9 is a right side sectional elevational view of another embodiment of the laryngoscope of this invention showing internal components.
Figure 10:
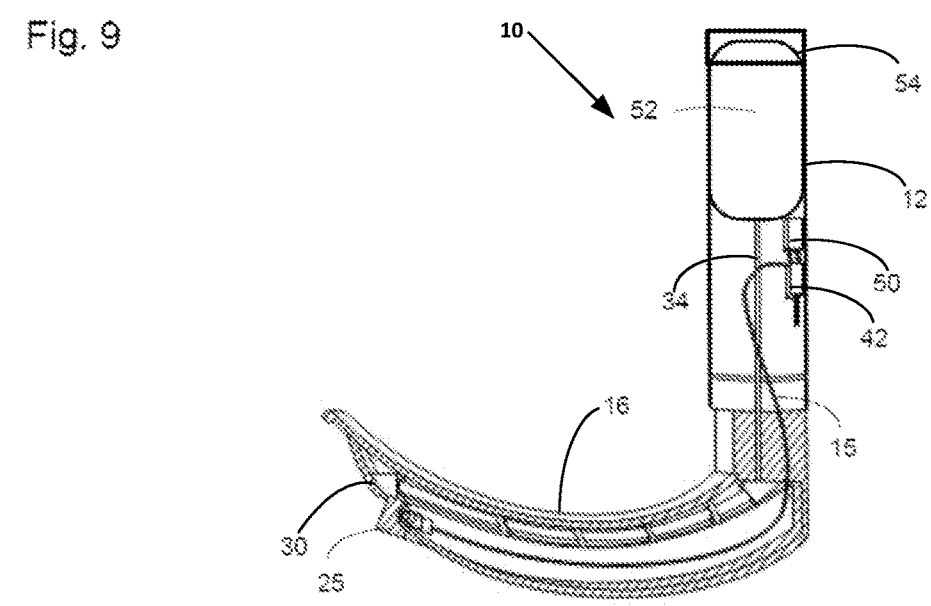
FIG. 10 is a right side sectional elevational view of another embodiment of the laryngoscope of this invention showing internal components.

In the alternative embodiments depicted in FIGS. 9 and 10, the laryngoscope may be physically untethered from external devices such as a monitor or an external source of cleansing liquid. Such alternative embodiments may be desirable in non-hospital environments when emergency situations call for immediate intubation under field conditions. In an embodiment shown in FIG. 10, video signals may be sent to an external monitor using a Bluetooth or comparable wireless medium utilizing a small transmission circuit 42. Power may be furnished to the LEDs and imaging device through a small, replaceable or rechargeable battery 50 situated in the handle.

Cleansing liquid may be held within a disposable or multiple-use bladder 52 internal to the laryngoscope, and can be delivered by applying pressure to the bladder 52 by a flexible, removable membrane 54 or through any other mechanism known in the art. These components may be enclosed within a removable handle 12, and may be used with a disposable blade 16. Connection of the handle 12 to the blade 16 can be achieved with a twisting or other conventional connection. Aligned contacts or external connectors may be used for electrical conductivity and fluid transfer, and all components within a handle may be maintained and replaced as necessary.

In field environments in which an external source of cleaning fluid is available (such as EMT vehicles), a leer-connection to such external source may be used to deliver the fluid to the laryngoscope, as indicated in FIG. 9.

While the present invention has been described in conjunction with preferred embodiments thereof, many modifications and variations will be apparent to those of ordinary skill in the art. For example, other conventional connections may be substituted for the luer-connection described herein; and other wireless communications systems may be used to transmit the image from the endoscopic camera to an external monitor. The foregoing description and the following claims are intended to cover all such modifications and variations.

What is claimed is:

1. A laryngoscope comprising:
   a handle defining an interior, a luer-compatible connection disposed within the interior of the handle and configured to couple to a removable syringe, a fluid channel disposed within the handle and configured to be in fluid communication with the removable syringe;
   a rigid curved blade having a fixed shape coupled to the handle;
   an aperture disposed near a distal end of the blade and configured to allow light to enter the blade;
   an imaging device at least partially enclosed by the blade and configured to capture light passing through the aperture;
   a transparent window configured to provide a physical barrier disposed across the aperture; and
   a fluid delivery line configured to deliver fluid from the fluid channel to an external surface of the transparent window.

2. The laryngoscope of claim 1, wherein the blade further comprises an illuminating element at least partially enclosed by the blade and configured to illuminate a target area of a surface exterior to the transparent window.

3. The laryngoscope of claim 1, wherein the blade further comprises a heating element at least partially enclosed by blade and configured to remove condensation from the transparent window.

4. The laryngoscope of claim 1, wherein the blade further comprises one or more light emitting diodes configured to remove condensation from the transparent window.

5. The laryngoscope of claim 1, wherein the luer-compatible connection is configured to align the removable syringe in parallel configuration with the handle.

6. The laryngoscope of claim 1, wherein the blade and the handle are integrally formed.

7. The laryngoscope of claim 1, wherein the blade and the handle are coupleable to one another.

8. The laryngoscope of claim 1, wherein fluid from the removable syringe is used to clean the transparent window.

9. A system comprising:
   the laryngoscope of claim 1; and
   the removable syringe.

* * * * *